United States Patent [19]  [11] 4,242,518
Rossy et al. [45] Dec. 30, 1980

[54] THIOPHENE COMPOUNDS AND THEIR MANUFACTURE

[75] Inventors: Phillip Rossy, Ludwigshafen; Werner Hoffmann, Neuhofen, both of Fed. Rep. of Germany

[73] Assignee: BASF Aktiengesellschaft, Fed. Rep. of Germany

[21] Appl. No.: 31,593

[22] Filed: Apr. 19, 1979

Related U.S. Application Data

[60] Division of Ser. No. 942,655, Sep. 15, 1978, which is a continuation of Ser. No. 784,571, Aug. 4, 1977, abandoned.

[30] Foreign Application Priority Data

Apr. 10, 1976 [DE]  Fed. Rep. of Germany ....... 2615885
Jan. 3, 1977 [DE]  Fed. Rep. of Germany ....... 2700215
Jan. 3, 1977 [DE]  Fed. Rep. of Germany ....... 2700262

[51] Int. Cl.³ .................. C07D 333/00; A61K 31/38; A23L 2/26

[52] U.S. Cl. ...................................... 549/61; 424/275; 426/535

[58] Field of Search ......................................... 549/61

[56] References Cited
PUBLICATIONS

Chem. Abst., vol. 78, (1973), 93630d.
Chem. Abst., vol. 84, (1976), 85612h.

*Primary Examiner*—Alan Siegel
*Attorney, Agent, or Firm*—Keil & Witherspoon

[57] ABSTRACT

New thiophene compounds and a new process for the manufacture of thiophene compounds by dehydrogenating dihydrothiophene with certain halogen compounds. The products are starting materials for the manufacture of pharmaceuticals, dyes and plant protection agents and, in particular, for the manufacture of additives to foodstuffs, feeds, beverages and pharmaceuticals.

1 Claim, No Drawings

THIOPHENE COMPOUNDS AND THEIR MANUFACTURE

This is a pending division of application Ser. No. 942,655, filed Sept. 15, 1978, which in turn is a continuation of application Ser. No. 784,571, filed Apr. 4, 1977, the latter of which is now abandoned.

The present invention relates to new thiophene compounds and to a new process for the manufacture of thiophene compounds by dehydrogenating dihydrothiophenes with certain halogen compounds.

Helv. Chim. Acta 57 (1974) 2,487–2,492 discloses that 4-hydroxy-5-phenyl-3-dihydrothiophenecarboxylic acid ethyl ester can be dehydrogenated with a large excess of hydrogen peroxide at an elevated temperature

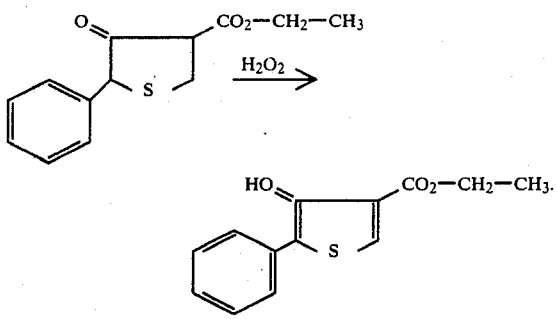

It has also been disclosed that dihydrothiophenes can be dehydrogenated with tetrachloroquinone (U.S. Patent 3,445,473). 1,4-Dihydro-4-methyl-thieno-[3,4-b]-quinolin-9-3H-one can be dehydrogenated with chloranil; the yield of end product is about 30% (Monatshefte der Chemie 105 (1974), 1,164–1,169). Monatshefte der Chemie, 106 (1975), 375–379 furthermore discloses that the reaction of 1,3,4,9-tetrahydro-thieno-[3,4-b][1,5]-benzo-diazepin-10-one with chloranil for 18 hours at 60° C. gives 4,9-dihydro-thieno[3,4-b][1,5]-benzodiazepin-10-one. The working up is involved and the yield obtained is only about 20%. As described in the said publication, variations in reaction time, reaction temperature and aromatizing agent either result in no reaction or give reaction mixtures which cannot be utilized for preparative purposes.

German Laid-Open Application DOS No. 1,945,964 discloses that 3-acetylamino-4,5-dihydrothiophene-2-ketones can be dehydrogenated with tetrachloroquinone, nitrosobenzene and iodosobenzene and, preferably, with selenium and sulfur. The starting materials are prepared by reacting α-halogenoketones with β-mercaptonitriles in the presence of basic condensing agents, and then cyclizing the thioethers formed. Sulfur is singled out particularly as a dehydrogenating agent and is used in most of the Examples.

German Published Application DAS No. 1,643,325 discloses that 3-diethylaminoacetylamino-2-carbomethoxy-4-methyl-4,5-dihydrothiophene can be dehydrogenated with chloranil or bromine. The yield, 54% of theory, is unsatisfactory. German Laid-Open Application DOS No. 2,537,070 discloses the reaction of 3-hydroxy-2-methoxycarbonylthiophene with phosphorus pentachloride in carbon tetrachloride, leading to 3-chlorothiophene-2-carboxylic acid (Example 1). A reaction of 3-keto-thiophane-4-carboxylic acid methyl ester with a large excess of phosphorus pentachloride for 17 hours also results in replacement of the keto group by a chlorine atom and gives 4-chloro-thiophene-3-carboxylic acid chloride (Example 5).

We have found that thiophene compounds of the formula

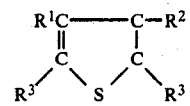   I and of the formula

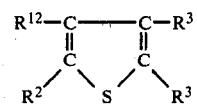   Ia where $R^1$ is

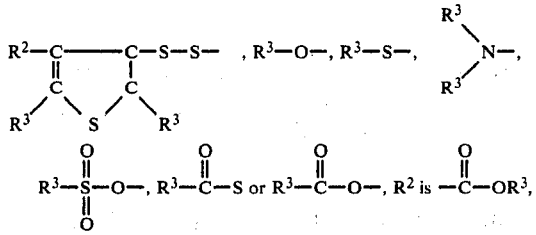

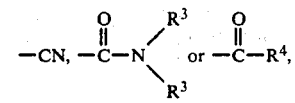

the individual radicals $R^3$ and $R^4$ may be identical or different and each is an aliphatic, cycloaliphatic, araliphatic or aromatic radical, and $R^3$ may also be hydrogen, $R^1$ and $R^2$ can also together be

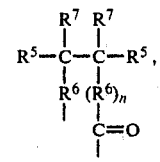

$R^5$ is hydrogen, the individual radicals $R^6$ may be identical or different and each is

—O— or —S—, the individual radicals $R^7$ may be identical or different and each is an aliphatic, cycloaliphatic, araliphatic or aromatic radical, the radicals $R^7$ may also, together with the radicals $R^5$ and the two adjacent carbon atoms, be members of an aromatic radical, $R^8$ is hydrogen or an aliphatic radical, n is 0 or 1 and $R^{12}$ has the meanings of $R^1$ or is

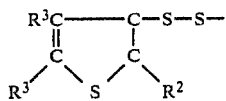

are obtained in an advantageous manner when dihydrothiophenes of the formula

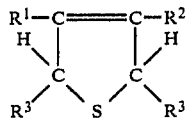

where $R^1$, $R^2$ and $R^3$ have the above meanings, are dehydrogenated with chlorides or bromides of phosphoric acid or sulfuric acid, with chlorine, bromine or iodine, or with N-halogen compounds of the formula

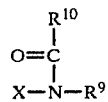

where X is chlorine or bromine, $R^9$ is hydrogen or

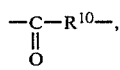

the individual radicals $R^{10}$ may be identical or different and each is an aliphatic, araliphatic or aromatic radical, the two radicals $R^{10}$ may also together be

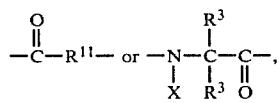

where $R^3$ and X have the above meanings and $R^{11}$ is alkylene, or when disulfido-(3,3')-bis-(dihydrothiophenes) of the formula

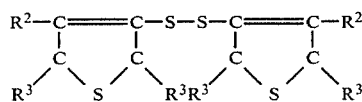

where $R^2$ and $R^3$ have the above meanings, or dihydrothiophenes of the formula

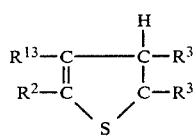

where $R^{13}$ has the meanings of $R^{12}$ or, if $R^{12}$ is

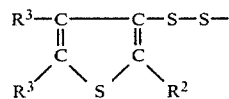

$R^{13}$ may also be

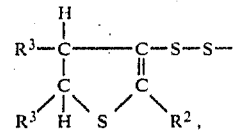

are dehydrogenated with chlorides or bromides of sulfuric acid or with chlorine.

We have also found the new thiophene compounds of the formula

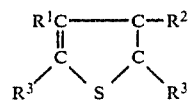

where $R^1$ is

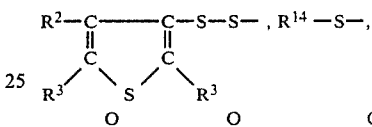

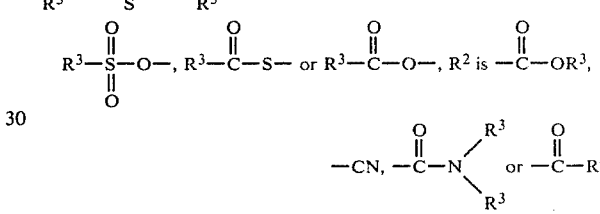

the individual radicals $R^{14}$, $R^3$ and $R^4$ may be identical or different and each is an aliphatic, cycloaliphatic, araliphatic or aromatic radical, but $R^{14}$ is of at least 2 carbon atoms if $R^2$ is —COOH, and $R^3$ may also be hydrogen and $R^1$ and $R^2$ may also together be

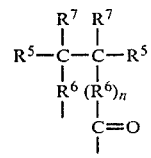

$R^5$ is hydrogen, the individual radicals $R^6$ may be identical or different and each is

—O— or —S—, the individual radicals $R^7$ may be identical or different and each is an aliphatic, cycloaliphatic, araliphatic or aromatic radical, the radicals $R^7$ may also, together with the radicals $R^5$ and the two adjacent carbon atoms, be members of an aromatic radical, $R^8$ is hydrogen or an aliphatic radical and n is 0 or 1, but $R^6$ is —O— or —S— if $R^7$ and $R^5$ are members of a phenylene ring and the two radicals $R^3$ on the thiophene ring are simultaneously each hydrogen, and $R^1$ may also be hydroxyl if $R^2$ is

Further, we have found the new thiophene compounds of the formula

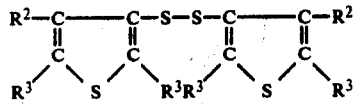   I where R² is

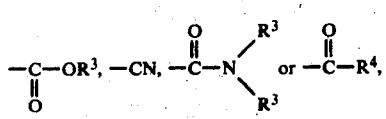

the individual radicals R³ and R⁴ may be identical or different and each is an aliphatic, cycloaliphatic, araliphatic or aromatic radical and R³ may also be hydrogen.

Further, we have found the new thiophene compounds of the formula

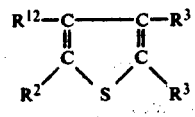   Ia where R¹² is R³—S—,

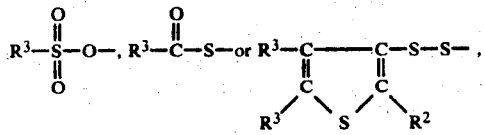

R² is

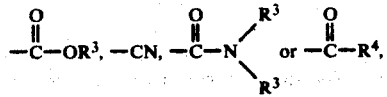

the individual radicals R³ and R⁴ may be identical or different and each is an aliphatic, cycloaliphatic, araliphatic or aromatic radical, and R³ may also be hydrogen.

Where 3-methoxy-4-carbomethoxy-thiophene and sulfuryl chloride are used, the reaction can be represented by the following equation:

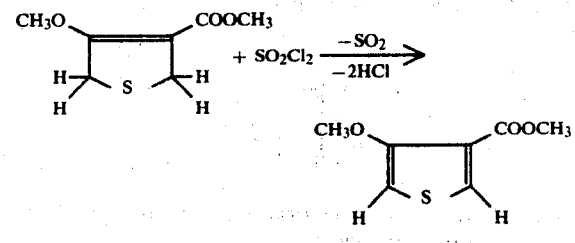

Where 3-methyl-sulfato-2-carbomethoxy-thiophene and sulfuryl chloride are used, the reaction can be represented by the following equation:

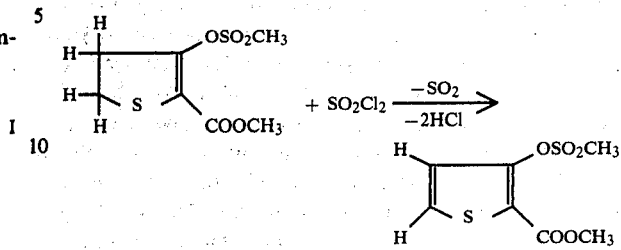

Where disulfido-(3,3')-bis-(4-carbomethoxydihydrothiophene) and sulfuryl chloride are used, the reaction can be represented by the following equation:

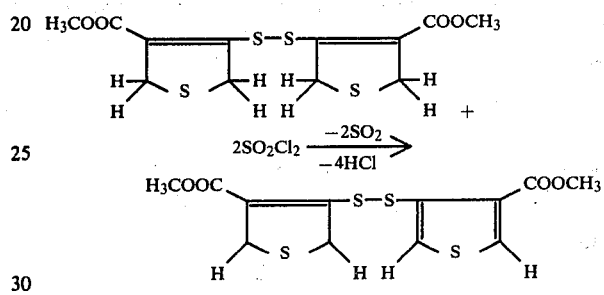

Compared to conventional processes, the process according to the invention surprisingly provides a large number of new and conventional thiophene compounds more simply and more economically, and in some cases in higher yield, better space-time yield and greater purity. Involved purification operations are avoided. In the context of German Laid-Open Application DOS No. 2,537,070 it is surprising that the 3-hydroxyl group and 3-keto group are not significantly replaced by chlorine.

The starting materials II, IIa or III can be obtained by conventional methods, for example from α,β-unsaturated carboxylic acids or their esters, amides or nitriles, by reaction with thioglycollic acid esters (U.S. Pat. No. 3,445,473), J. Amer. Chem. Soc. 68 (1946), 2,229–2,235, and Monatshefte der Chemie 104 (1973), 1,520–1,525), by reacting β-mercaptopropionic acid esters with α-haloacetic acid derivatives or their esters or amides or α-haloketones, for example α-chloroacetophenone, by the method disclosed in German Laid-Open Application DOS No. 1,945,964 or by reacting 3-oxo-tetrahydro-thiophenes (Organic Reactions VI, 443–468), with diazoalkanes, or by reacting the enolate salts with suitable alkylating reagents or acylating reagents, e.g. alkyl halides, acid anhydrides or sulfonyl halides. Starting amines II or III can also be obtained by reacting suitable compounds from amongst those mentioned above with amines in the presence of a catalyst, e.g. p-toluene-sulfonic acid (U.S. Pat. No. 3,445,473). Thus, they can be manufactured from a starting material II or III, containing sulfonate groups, by reaction with the desired amine. Thiol derivatives II are obtained by reaction with hydrogen sulfide in an inert solvent; the thioketones formed can be alkylated or acylated by conventional methods (Ber. 100 (1967), 93–100). Similarly, starting materials III containing sulfonate groups can be converted to starting thiol derivatives III by reaction with thiols. The thiophenes thus obtained can, directly or after conversion to the corresponding 3-toluene-sulfonylthiophenes or 3-sulfato-thiophenes, be reacted with disulfide compounds, e.g. disodium disulfide, to give the starting materials III (Org. Syn. Coll. Vol. 2, 580 (1943); German Published Application DAS No. 1,805,778; Houben-Weyl, Methoden der Organischen Chemie, Volume 9, pages 55–82). Examples 13a and 13b show a suitable process for the manufacture of the starting materials IIa. The process disclosed in German patent application No. P 27 00 261.5 can also be used for the manufacture of dihydrodisulfido-thiophenes III. In addition, reference may be made, in connection with the manufacture of the starting materials II or III, to the cited prior art publications.

Preferred starting materials II, IIa and III and, accordingly, preferred end products I and Ia are those in which $R^1$ is

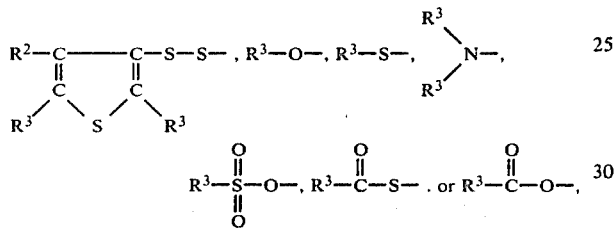

$R^{12}$ has the meanings of $R^1$ or is

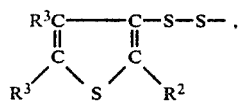

$R^2$ is

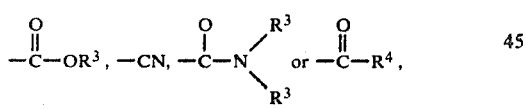

the individual radicals $R^{14}$, $R^3$ and $R^4$ are identical or different and each is alkyl of 1 to 7 carbon atoms, cycloalkyl of 5 to 7 carbon atoms, aralkyl of 7 to 12 carbon atoms or phenyl, but $R^{14}$ is of at least 2 carbon atoms if $R^2$ is —COOH, and is advantageously alkyl of 2 to 7 carbon atoms, and $R^3$ in many cases is advantageously of at least 2 carbon atoms if $R^2$ is —COOH, and is advantageously alkyl of 2 to 7 carbon atoms, and $R^3$ may also be hydrogen or, if $R^{12}$ is

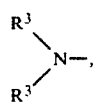

$R^3$ may also be acyl, advantageously alkanecarbonyl of 2 to 7 carbon atoms, $R^{13}$ has the meanings of $R^{12}$ or, if $R^{12}$ is

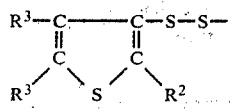

$R^{13}$ may also be

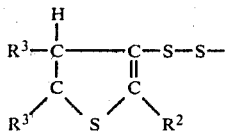

$R^1$ and $R^2$ may also together be

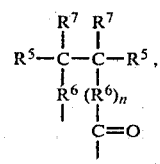

$R^5$ is hydrogen, the individual radicals $R^6$ may be identical or different and are each

—O— or —S—, the individual radicals $R^7$ may be identical or different and each is alkyl of 1 to 7 carbon atoms, cycloalkyl of 5 to 7 carbon atoms, aralkyl of 7 to 12 carbon atoms or phenyl, the radicals $R^7$ may also, together with the radicals $R^5$ and the two adjacent carbon atoms, be members of a phenylene radical, $R^8$ is hydrogen or alkyl of 1 to 7 carbon atoms and n is 0 or 1. The 3-hydroxy compound II

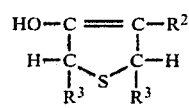

can also be used in the form of the tautomeric 3-oxo-4-tetrahydro compound II

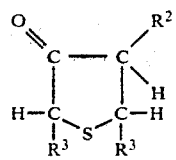

The 3-hydroxy compound III

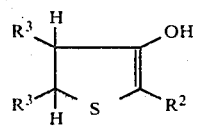

can also be used in the form of the tautomeric 3-oxo-2-tetrahydro compound III

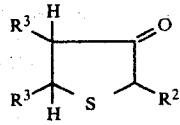

The above radicals may in addition be substituted by groups or atoms which are inert under the reaction conditions, e.g. carbalkoxy of 2 to 4 carbon atoms, alkyl and alkoxy each of 1 to 4 carbon atoms, carboxyl, nitrile, or chlorine atoms present as substituents of the phenyl radicals.

Examples of suitable starting materials II are: 4-ethoxycarbonyl-, 4-methoxycarbonyl-, 4-n-butoxycarbonyl-, 4-tert.-butoxycarbonyl-, 4-sec.-butoxycarbonyl-, 4-propoxycarbonyl-, 4-isobutoxycarbonyl-, 4-isopropoxycarbonyl-, 4-phenoxycarbonyl-, 4-benzyloxycarbonyl-, 4-cyclohexanoxycarbonyl- and 4-nitrilo-3-hydroxy-dihydrothiophene; (N-methyl)-, (N-ethyl)-, (N-propyl)-, (N-isopropyl)-, (N-butyl)-, (N-isobutyl)-, (N-sec.-butyl)-, (N-tert.-butyl)-, (N-phenyl)-, (N-benzyl)- and (N-cyclohexyl)-4-carboxamido-3-hydroxy-dihydrothiophene; (N,N-dimethyl)-, (N,N-diethyl)-, (N,N-dipropyl)-, (N,N-diisopropyl)-, (N,N-dibutyl)-, (N,N-di-sec.-butyl)-, (N,N-di-tert.-butyl)-, (N,N-diisobutyl)-, (N,N-diphenyl)-, (N,N-dibenzyl)- and (N,N-dicyclohexyl)-4-carboxamido-3-hydroxy-dihydrothiophene; 4-methylcarbonyl-, 4-ethylcarbonyl-, 4-propylcarbonyl-, 4-butylcarbonyl-, 4-isopropyl-carbonyl-, 4-cyclohexanecarbonyl-, 4-benzoylcarbonyl-, 4-phenylacetyl-, 4-carboxamido- and 4-carboxy-3-hydroxy-dihydrothiophene; analogous 3-methoxy-, 3-ethoxy-, 3-propoxy-, 3-isopropoxy-, 3-butoxy-, 3-isobutoxy-, 3-tert.-butoxy-, 3-sec.-butoxy-, 3-phenoxy-, 3-benzoxy-, 3-cyclohexoxy-, 3-methylthio-, 3-ethylthio-, 3-propylthio-, 3-isopropylthio-, 3-butylthio-, 3-isobutylthio-, 3-sec.-butylthio-, 3-tert.-butylthio-, 3-phenylthio-, 3-benzylthio- and 3-cyclohexylthio compounds; analogous 3-aminothiophenes and 3-amino compounds monosubstituted or disubstituted at the nitrogen by methyl, ethyl, propyl, isopropyl, butyl, isobutyl, sec.-butyl, tert.-butyl, phenyl, benzyl or cyclohexyl; analogous 3-methyl-, 3-ethyl-, 3-propyl-, 3-isopropyl-, 3-butyl-, 3-isobutyl-, 3-sec.-butyl-, 3-tert.-butyl-, 3-cyclohexyl-, 3-phenyl- and 3-benzyl-sulfatothiophenes, 3-methyl-, 3-ethyl-, 3-propyl-, 3-isopropyl-, 3-butyl-, 3-isobutyl-, 3-sec.-butyl-, 3-tert.-butyl-, 3-phenyl-, 3-benzyl- and 3-cyclohexyl-carbonylthio compounds and corresponding carbonyloxy compounds; dehydro-thieno-[3,4-b]-quinolin-9(3H)-one and corresponding 4-methyl- and 4-ethylquinolinones, thienochromanones and thienothiochromanones; and dihydrothiophenes analogous to the above dihydrothiophenes but mono-substituted in the 2-position or 5-position, or disubstituted in the 2-position and 5-position, by methyl, ethyl, propyl, isopropyl, butyl, isobutyl, sec.-butyl, tert.-butyl, phenyl, benzyl or cyclohexyl.

The following are examples of suitable starting materials IIa (in determining the positions of the substituents, the figures run anti-clockwise in the left-hand thiophene nucleus and clockwise in the right-hand thiophene nucleus): disulfido-(3,3')-bis-(dihydrothiophenes) substituted in the 4-position and 4'-position of the two dihydrothiophene nuclei by the ethoxycarbonyl, methoxycarbonyl, n-butoxycarbonyl, tert.-butoxycarbonyl, sec.-butoxycarbonyl, propoxycarbonyl, isobutoxycarbonyl, isopropoxycarbonyl, phenoxycarbonyl, benzyloxycarbonyl, cyclohexanoxycarbonyl or nitrile group; disulfido-(3,3')-bis-(dihydrothiophenes) substituted in the 4-position and 4'-position of the two dihydrothiophene nuclei by the (N-methyl)-, (N-ethyl)-, (N-propyl)-, (N-isopropyl)-, (N-butyl)-, (N-isobutyl)-, (N-sec.-butyl)-, (N-tert.-butyl)-, (N-phenyl)-, (N-benzyl)- or (N-cyclohexyl)-carboxamido group; disulfido-(3,3')-bis-(dihydrothiophenes) substituted in the 4-position and 4'-position of the two dihydrothiophene nuclei by the (N,N-dimethyl)-, (N,N-diethyl)-, (N,N-dipropyl)-(N,N-diisopropyl)-, (N,N-dibutyl)-, (N,N-di-sec.-butyl)-, (N,N-di-tert.-butyl)-, (N,N-diisobutyl)-, (N,N-diphenyl)-, (N,N-dibenzyl)- or (N,N-dicyclohexyl)-carboxamido group; disulfido-(3,3')-bis-(dihydrothiophenes) substituted in the 4-position and 4'-position of the two dihydrothiophene nuclei by the methylcarbonyl, ethylcarbonyl, propylcarbonyl, butylcarbonyl, sec.-butylcarbonyl, isobutylcarbonyl, tert.-butylcarbonyl, isopropylcarbonyl, cyclohexanecarbonyl, benzoyl, phenylacetyl, carboxamido or carboxyl group; and dihydrothiophenes, analogous to the above dihydrothiophenes, which are disubstituted in the 2-position and 2'-position or 5-position and 5'-position, or tetrasubstituted in the 2-position, 2'-position, 5-position and 5'-position, by methyl, ethyl, propyl, isopropyl, butyl, isobutyl, sec.-butyl, tert.-butyl, phenyl, benzyl or cyclohexyl groups.

Examples of suitable starting materials III are: 2-ethoxycarbonyl-, 2-methoxycarbonyl-, 2-n-butoxycarbonyl-, 2-tert.-butoxycarbonyl-, 2-sec.-butoxycarbonyl-, 2-propoxycarbonyl-, 2-isobutoxycarbonyl-, 2-isopropoxycarbonyl-, 2-phenoxycarbonyl-, 2-benzyloxycarbonyl-, 2-cyclohexanoxycarbonyl- and 2-nitrilo-3-hydroxy-dihydrothiophene; (N-methyl)-, (N-ethyl)-, (N-propyl)-, (N-isopropyl)-, (N-butyl)-, (N-isobutyl)-, (N-sec.-butyl)-, (N-tert.-butyl)-, (N-phenyl)-, (N-benzyl)- and (N-cyclohexyl)-2-carboxamido-3-hydroxy-dihydrothiophene; (N,N-dimethyl)-, (N,N-diethyl)-, (N,N-dipropyl)-, (N,N-diisopropyl)-, (N,N-dibutyl)-, (N,N-di-sec.-butyl)-, (N,N-di-tert.-butyl)-, (N,N-diisobutyl)-, (N,N-diphenyl)-, (N,N-dibenzyl)- and (N,N-dicyclohexyl)-2-carboxamido-3-hydroxy-dihydrothiophene; 2-methylcarbonyl-, 2-ethylcarbonyl-, 2-propylcarbonyl-, 2-butylcarbonyl-, 2-isopropylcarbonyl-, 2-cyclohexanylcarbonyl-, 2-benzylcarbonyl-, 2-phenylacetyl-, 2-carboxamido- and 2-carboxy-3-hydroxy-dihydro-thiophene; analogous 3-methoxy-, 3-ethoxy-, 3-propoxy-, 3-isopropoxy-, 3-butoxy-, 3-isobutoxy-, 3-tert.-butoxy-, 3-sec.-butoxy-, 3-phenoxy-, 3-benzoxy-, 3-cyclohexoxy-, 3-methylthio-, 3-ethylthio-, 3-propylthio-, 3-isopropylthio-, 3-butylthio-, 3-isobutylthio-, 3-sec.-butylthio-, 3-tert.-butylthio-, 3-phenylthio-, 3-benzylthio- and 3-cyclohexylthio compounds; analogous 3-aminothiophenes, and 3-amino compounds mono-substituted or disubstituted at the nitrogen by methyl, ethyl, propyl, isopropyl, butyl, isobutyl, sec.-butyl, tert.-butyl, phenyl, benzyl or cyclohexyl; analogous 3-methyl-, 3-ethyl-, 3-propyl-, 3-isopropyl-, 3-butyl-, 3-isobutyl-, 3-sec.-butyl-, 3-tert.-butyl-, 3-cyclohexyl-, 3-phenyl- and 3-benzylsulfatothiophenes and 3-methyl-, 3-ethyl-, 3-propyl-, 3-isopropyl-, 3-butyl-, 3-isobutyl-, 3-sec.-butyl-, 3-tert.-butyl-, 3-phenyl-, 3-benzyl- and 3-cyclohexyl-carbonylthio compounds and corresponding 3-carbonyloxy compounds; dehydrothiene-[2,3-b]-quinolinone and corresponding N-methyl- and N-ethyl-quinolinones, thienochromanones and thienothiochromanones; dihydrothiophenes, analogous to the above dihydrothiophenes, which are monosubstituted in the 4-position or 5-position, or disubstituted in the 4-position and 5-position, by methyl, ethyl, propyl, isopropyl, butyl, isobutyl, sec.-butyl, tert.-butyl, phenyl, benzyl or cyclohexyl.

The starting materials II, IIa or III are reacted with a stoichiometric amount of the dehydrogenating agents according to the invention or with an excess of the latter agents, preferably with from 1 to 2, especially from 1 to 1.1, equivalents of dehydrogenating agent, per mole of starting material II. Examples of dehydrogenating agents, for the case of the starting materials II, are phosphorus pentabromide, phosphorus pentachloride, sulfuryl chloride, sulfuryl bromide, chlorine, bromine and iodine; N-halogen compounds IV, where X is chlorine or bromine, $R^9$ is hydrogen or

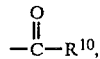

the individual radicals $R^{10}$ may be identical or different and each is alkyl of 1 to 6 carbon atoms, aralkyl or 7 to 12 carbon atoms or phenyl, the two radicals $R^{10}$ together may also be

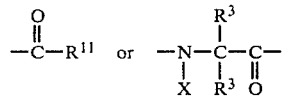

where the individual radicals $R^3$ may be identical or different and each is alkyl of 1 to 7 carbon atoms, cycloalkyl of 5 to 7 carbon atoms, aralkyl of 7 to 12 carbon atoms, phenyl or hydrogen, X is chlorine or bromine, and $R^{11}$ is alkylene of 2 to 4 carbon atoms. Examples of advantageous dehydrogenating agents, for the case of the starting materials II, are sulfuryl chloride, sulfuryl bromide, chlorine, bromine, iodine, chlorosuccinimide, bromosuccinimide, N-chloroglutarimide, N-bromoglutarimide, N-chloroadipimide, N-bromoadipimide, N-bromoacetamide, N-chloroacetamide, N-chlorobenzoylamide, N-bromobenzoylamide, N-chloro-(N-acetyl)-acetamide, N-bromo-(N-acetyl)-acetamide, N,N'-dibromohydantoin, N,N'-dichlorohydantoin, N,N'-dibromo-5,5-dimethylhydantoin, N,N'-dichloro-5,5-dimethylhydantoin, N,N'-dibromo-5,5-diphenylhydantoin and N,N'-dichloro-5,5-diphenylhydantoin; the most preferred dehydrogenating agents are, as in the case of the starting materials IIa and III, sulfuryl chloride, sulfuryl bromide and chlorine.

The reaction is as a rule carried out at from $-30°$ to $+100°$ C., preferably from $+10°$ to $+40°$ C., under reduced pressure or superatmospheric pressure or, preferably, under atmospheric pressure, continuously or batchwise. It is advantageous to use organic solvents which are inert under the reaction conditions, such as aromatic hydrocarbons, for example toluene, ethylbenzene, o-, m- and p-xylene, isopropylbenzene and methylnaphthalene; halohydrocarbons, especially chlorohydrocarbons, e.g. tetrachloroethylene, 1,1,2,2- or 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, tetrachloroethane, 1,1,1- or 1,1,2-trichloroethane, trichloroethylene, pentachloroethane, cis-dichloroethylene, o-, m- and p-difluorobenzene, 1,2-dichloroethane, 1,1-dichloroethane, n-propyl chloride, 1,2-cisdichloroethylene, n-butyl chloride, 2- and 3-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane; ethers, e.g. ethyl propyl ether, methyl tert.-butyl ether, n-butyl ethyl ether, di-n-butyl ether, diisobutyl ether, diisoamyl ether, diisopropyl ether, anisole, phenetol, cyclohexyl methyl ether, diethyl ether, ethylene glycol dimethyl ether, tetrahydrofuran, dioxane, thioanisole and $\beta,\beta'$-dichlorodiethyl ether; aliphatic or cycloaliphatic hydrocarbons, e.g. heptane, pinane, nonane, gasoline fractions having a boiling range of from 70° to 190° C., cyclohexane, methylcyclohexane, petroleum ether, decalin, pentane, hexane, naphtha, 2,2,4-trimethylpentane, 2,2,3-trimethylpentane, 2,3,3-trimethylpentane and octane; dimethylformamide; and mixtures of the above. The solvent is advantageously used in an amount of from 400 to 10,000 percent by weight, preferably of from 400 to 2,000 percent by weight, based on starting material II, IIa or III. In the case of starting materials II and III it is at times advantageous to carry out the reaction under exposure to a source of light of from 2,000 to 8,000 Å. Auxiliaries such as azo-bis-isobutyronitrile may also be added, advantageously in amounts of from 1 to 5% by weight, based on starting material II or III.

The reaction is advantageously carried out in the presence of a stoichiometric amount or an excess of an acid-binding agent, suitable amounts being from 1.9 to 2.1 equivalents of acid-binding agent per mole of starting material II, IIa or III. Preferred acid-binding agents are tertiary amines, alkaline earth metal compounds, ammonium compounds and especially alkali metal compounds, as well as mixtures of these. Advantageous alkali metal compounds and alkaline earth metal compounds to use are the hydroxides, oxides, carbonates, bicarbonates, salts of weak or polybasic acids, and alcoholates of calcium, barium, magnesium, lithium and, especially, sodium and potassium. Examples of suitable basic compounds are potassium hydroxide, sodium hydroxide, potassium carbonate, sodium carbonate, potassium bicarbonate, calcium hydroxide, barium oxide, magnesium hydroxide, calcium carbonate, sodium acetate, propionate, ethylene-glycollate, methylate, propylate, isopropylate, ethylate and tripropylene-glycollate, potassium tert.-butylate, trimethylamine, triethylamine, pyridine, diethylaniline, dimethylaminoethanol, Nethylpiperidine, N-methylpyrrolidine, dimethylaniline, quinoline and N-methylpyrrolidone. Basic ion exchangers may also be used to bind the acid.

The reaction may be carried out as follows: a mixture of the starting material II, IIa or III, of the dehydrogenating agent and, where appropriate, of the solvent is kept for from 0.5 to 3 hours at the reaction temperature. The end product is then isolated from the mixture by conventional methods, for example by extraction with one of the above solvents or by washing with alkali, e.g. with a sodium carbonate solution, and distilling the organic phase.

The thiophene compounds which may be manufactured by the process of the invention are valuable starting materials for the manufacture of pharmaceuticals, dyes and plant protection agents and especially for the manufacture of additives for foodstuffs, feeds, beverages and pharmaceuticals. All end products containing the above preferred radicals are particularly suitable for the said use. For details of the use, reference may be made to the above literature and to Ullmanns Encyklopädie der technischen Chemie, volume 17, page 354. By way of example, the disulfidothiophenes I can be converted by chlorination, for example in a mixture of chloroform and water at from 0° to 20° C., to give the corresponding 3-chlorosulfonylthiophenes, from which the thiophene-saccharines described in German Laid-Open Application DOS No. 2,534,689, and used as sweeteners, may be manufactured by reacting with ammonia to give the corresponding 3-sulfonamido compounds, which are then cyclized. 3-Chlorosulfonylthiophenes are used as intermediates for the manufacture of analgesics (German Laid-Open Applicaion DOS No. 2,537,070).

In the Examples which follow, parts are by weight and bear the same relation to parts by volume as that of the kilogram to the liter.

EXAMPLE 1

(a) (Manufacture of the starting material): 3-methoxycarbonylmethylthiopropionic acid methyl ester

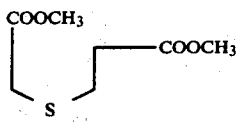

849 parts of thioglycollic acid methyl ester and 8 parts of piperidine are introduced into a stirred vessel and are cooled to 10°–15° C. 758 parts of methyl acrylate are added in the course of 2 hours, at from 40° to 50° C. During the reaction, a further 4 parts of piperidine are added twice. After completion of the addition, the reaction mixture is heated for 10 minutes at 60° C. and is then distilled under reduced pressure from a waterpump. 1,461 parts (95% of theory) of 3-methoxycarbonylmethylthiopropionic acid methyl ester of boiling point 142°–144° C./1.4 mbar are obtained.

(b) Manufacture of the starting material): 3-hydroxydihydrothiophene-4-carboxylic acid methyl ester

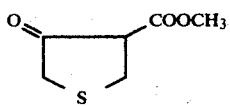

192 parts of 3-methoxycarbonylmethyl-thiopropionic acid methyl ester are added in the course of 10 minutes to a boiling solution of 540 parts of a 30 percent strength by weight NaOCH₃/MeOH solution, and the mixture is refluxed for 30 minutes and cooled to room temperature. The solution obtained is poured onto a mixture of 175 parts of concentrated hydrochloric acid and 1,000 parts of finely crushed ice. The oily layer which separates out is removed and the aqueous phase is extracted with five times 100 parts by volume of methylene chloride. The combined organic phases are extracted with twice 100 parts by volume of saturated NaHCO₃ solution, dried over sodium sulfate and evaporated. The residue is distilled and recrystallized from methanol. 70 parts (44% of theory) of 3-hydroxy-dihydrothiophene-4-carboxylic acid methyl ester, melting point 38°–41° C. and boiling point 63°–64° C./0.01 mbar, are obtained.

(c) (Reaction): 3-hydroxy-thiophene-4-carboxylic acid methyl ester

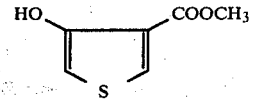

80 parts of 3-hydroxy-dihydrothiophene-4-carboxylic acid methyl ester are dissolved in 800 parts by volume of methylene chloride. 74.3 parts of sulfuryl chloride in 200 parts by volume of methylene chloride are added in the course of one hour at from 10° to 15° C., whilst passing nitrogen into the mixture. The mixture is then stirred for 30 minutes at from 10° to 15° C., after which it is extracted by shaking with 500 parts of water and 300 parts by volume of a 5 percent strength by weight sodium bicarbonate solution. The organic phase is dried and evaporated. The residue is distilled. 60.5 parts (77% of theory) of 3-hydroxy-thiophene-4-carboxylic acid methyl ester of boiling point 76°–84° C./0.07–0.1 mbar are obtained.

EXAMPLE 2

(a) (Manufacture of the starting material): 3-methoxy-dihydrothiophene-4-carboxylic acid methyl ester

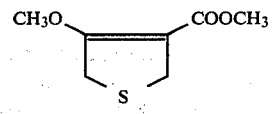

15 parts by volume of an 0.5 molar solution of diazomethane in ether are added in the course of about 10 minutes to a solution, cooled to 0° C., of 1.6 parts of 3-oxo-tetrahydrothiophene-4-carboxylic acid methyl ester in 10 parts by volume of dry chloroform. The solution is stirred for 21 hours at 0° C., flushed with nitrogen to remove excess diazomethane and concentrated under reduced pressure. The residue is recrystallized from methylene chloride/petroleum ether. 1.5 parts (86% of theory) of 3-methoxy-dihydrothiophene-4-carboxylic acid methyl ester of melting point 79°–81° C. are obtained.

(b) (Reaction): 3-methoxythiophene-4-carboxylic acid methyl ester

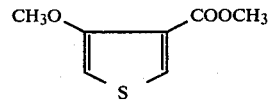

15 parts by volume of a Cl₂/CCl₄ solution (7.1 parts of chlorine in 100 parts of CCl₄) are added in the course of 10 minutes to a solution, cooled to 0° C., of 1.74 parts of 3-methoxy-dihydrothiophene-4-carboxylic acid methyl ester in 15 parts by volume of CCl₄. The mixture is kept at 0° C. for one hour. The end product is isolated from the reaction mixture by the method described in Example 1c. 1.6 parts (93% of theory) of 3-methoxythiophene-4-carboxylic acid methyl ester of melting point 66°–67° C. are obtained.

EXAMPLE 3

(a) (Manufacture of the starting material): 3-hydroxy-4-cyanodihydrothiophene

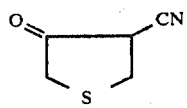

A mixture of 216 parts of acrylonitrile and 430 parts of thioglycollic acid methyl ester is added to a solution of sodium methylate (132 parts of sodium in 1,800 parts of methanol) at 20° C. The solution is heated under reflux for one hour and cooled, and the mixture is filtered after 12 hours at 0° C. The filter residue is dissolved in 250 parts of water, the solution is acidified with dilute hydrochloric acid at 0° C., the mixture is then extracted three times with methylene chloride and the combined organic phases are dried over sodium sulfate and concentrated. 300 parts (60% of theory) of 3-hydroxy-dihydrothiophene-4-carboxylic acid nitrile of melting point 70°–72° C. are obtained.

(b) Manufacture of the starting material): 3-methyl-sulfato-4-cyanodihydrothiophene

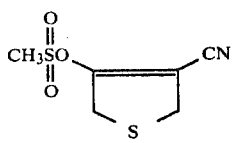

1.27 parts of 3-hydroxy-dihydrothiophene-4-carboxylic acid nitrile and 0.86 part by volume of methanesulfonic acid chloride are dissolved in 10 parts by volume of pyridine at 0° C. The resulting solution is stirred for 15 hours at 0° C. After the reaction, the mixture is poured into 50 parts by volume of ice water and the batch is extracted with three times 50 parts by volume of methylene chloride. The combined organic phases are washed with twice 50 parts by volume of 10 percent strength by weight aqueous citric acid solution and three times with saturated sodium chloride solution. After drying and concentrating the organic phases, 1.8 parts (85% of theory) of 3-methylsulfato-4-cyanodihydrothiophene of melting point 80.5°–82° C. are obtained.

(c) (Reaction): 3-methylsulfato-4-cyanothiophene

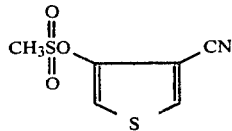

2.05 parts of 3-methylsulfato-4-cyano-dihydrothiophene are dissolved in 30 parts by volume of dry methylene chloride. 0.88 part of sulfuryl chloride in 5 parts by volume of methylene chloride are added at 0° C., whilst passing nitrogen into the mixture, and stirring is continued for 30 minutes. The end product is isolated from the reaction mixture by the method described in Example 1c. 1.85 parts (90% of theory) of 3-methylsulfato-4-cyanothiophene of melting point 52°–55° C. are obtained.

EXAMPLE 4

(a) (Manufacture of the starting material): 3-(2',6'-dichloroanilino)-4-cyano-dihydrothiophene

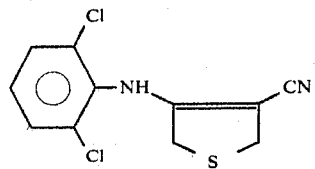

8.1 parts of 2,6-dichloro-aniline, 6.3 parts of 3-hydroxydihydrothiophene-4-carboxylic acid nitrile and 100 parts of p-toluenesulfonic acid are dissolved in 60 parts by volume of toluene and the mixture is boiled for 4 hours under reflux. 30 parts by volume of toluene are distilled off, and the warm solution is filtered and left to stand at room temperature. 9 Parts (67% of theory) of 3-(2',6'-dichloroanilino)-4-cyano-dihydrothiophene of melting point 170°–173° C. are obtained.

(b) (Reaction):
3-(2',6'-dichloro-4-cyanothiophene

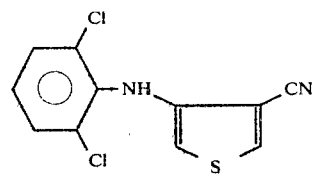

A solution of 0.27 part of 3-(2',6'-dichloro-anilino)-4-cyanodihydrothiophene in 15 parts by volume of dry methylene chloride is added, in the course of 30 minutes, to a solution of 0.12 part by volume of sulfuryl chloride in 15 parts by volume of dry methylene chloride at 0° C. The end product is isolated from the reaction mixture by the method described in Example 1c. 0.20 (75% of theory) of 3-(2',6'-dichloroanilino)-4-cyanothiophene of melting point 105°–108° C. are obtained.

EXAMPLE 5

(a) (Manufacture of the starting material): α-carbomethoxy-methyl β'-acetyl ethyl sulfide

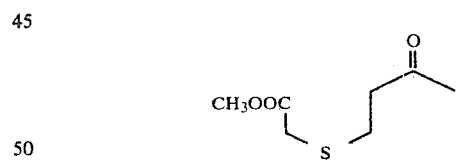

7 parts of methyl vinyl ketone are added to a mixture of 10 parts of thioglycollic acid methyl ester and 0.5 part of piperidine at room temperature. The reaction mixture is then stirred for 3 hours at 70° C., cooled, washed with water, dried and distilled. 12 parts (72% of theory) of α-carbomethoxy-β'-acetylmethylethyl-sulfide of boiling point 143° C./1.2 mbar are obtained.

(b) (Manufacture of the starting material): 3-hydroxy-4-acetyl-dihydrothiophene

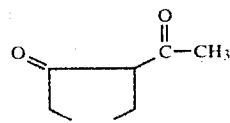

12 parts of α-carbomethoxy-β'-acetylmethylethylsulfide are added in the course of 10 minutes to a solution, at 70° C., or 300 parts by volume of toluene and 3.5 parts of sodium methylate, and the mixture is stirred for 3 hours at 70° C. After cooling, the mixture is added to 100 parts by volume of ice water and 8 parts by volume of glacial acetic acid. The toluene phase is washed with 200 parts by volume of 10 percent strength by weight NaOH. The alkaline phase is acidified with 30 parts by volume of glacial acetic acid and extracted with ether. The ether phase is dried, concentrated and distilled under reduced pressure. 2.5 parts (32% of theory) of 3-hydroxy-4-acetyl-dihydrothiophene of boiling point 119° C./1.2 mbar are obtained.

(c) (Reaction): 3-hydroxy-4-acetylthiophene

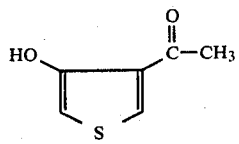

2.88 parts of 3-hydroxy-4-acetyldihydrothiophene are introduced into 20 parts by volume of dried methylene chloride; a solution of 1.7 parts by volume of sulfuryl chloride in 20 parts by volume of dried methylene chloride is added in the course of 10 minutes at 0° C. During the reaction, nitrogen is passed in, in order to expel the hydrochloric acid formed. After 30 minutes, the reaction mixture is worked up. The end product is isolated from the reaction mixture by the method described in Example 1c. 2.22 parts (77% of theory) of 3-hydroxy-4-acetylthiophene of melting point 44°–47° C. are obtained.

EXAMPLE 6

3-Hydroxythiophene-4-carboxylic acid methyl ester

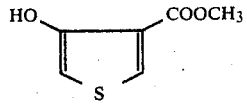

1.6 parts of 3-hydroxy-dihydrothiophene-4-carboxylic acid methyl ester are introduced into 15 parts by volume of carbon tetrachloride and the mixture is cooled to 0° C. 1.78 parts of N-bromosuccinimide are added in portions over 30 minutes and the mixture is kept for one hour at 0° C. The end product is isolated from the reaction mixture analogously to Example 5c. 1.2 parts (76% of theory) of 3-hydroxythiophene-4-carboxylic acid methyl ester of melting point 40°–43° C. are obtained.

EXAMPLE 7

(a) (Manufacture of the starting material): 3-phenylthio-4-dihydrothiophene-nitrile

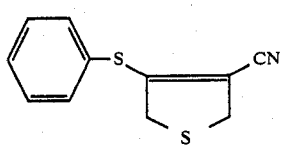

10.25 parts of 3-methylsulfato-4-cyanodihydrothiophene are introduced into 100 parts by volume of dimethylformamide and the mixture is cooled to 0° C. 9.9 parts of sodium thiophenolate in 50 parts by volume of dimethylformamide are added in the course of 15 minutes and stirring is continued for 30 minutes at 0° C. The end product is isolated from the reaction mixture by the method described in Example 5c. 9.3 parts (85% of theory) of 3-phenylthio-4-dihydrothiophene-nitrile of melting point 79.5°–81° C. are obtained.

(b) (Reaction): 3-phenylthio-4-thiophene-nitrile

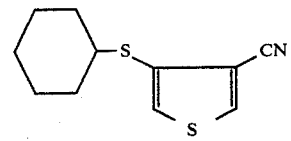

3.6 parts by volume of sulfuryl chloride in 25 parts by volume of methylene chloride are added, at 0° C., to a solution of 8.76 parts of 3-phenylthio-4-dihydrothiophene-nitrile in 100 parts by volume of methylene chloride. During the reaction, nitrogen is passed into the mixture. The end product is isolated from the reaction mixture by the method described in Example 5c. 7.8 parts (90% of theory) of 3-phenylthio-4-thiophene-nitrile of melting point 32°–34° C. are obtained.

EXAMPLE 8

3-Methyl-thieno-[3,4-b]-quinolin-9(4H)-one

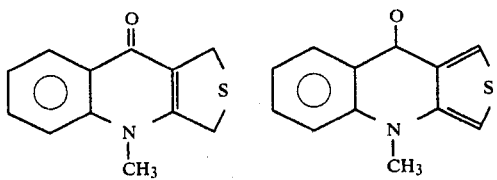

2.17 parts of 1,4-dihydro-4-methylthieno-[3,4-b]-quinolin-9(3H)-one are reacted with 0.88 part by volume of sulfuryl chloride in 25 parts by volume of methylene chloride at 0° C. for 0.5 hour. The end product is isolated from the reaction mixture by the method described in Example 5c. 1.50 parts (70% of theory) of 4-methylthieno-[3,4-b]-quinolin-9(4H)-one of the melting point 188°–190° C. are obtained.

EXAMPLE 9

(a) (Manufacture of the starting material): 3-hydroxy-5-methyldihydrothiophene-4-carboxylic acid methyl ester

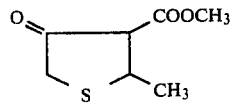

54 parts of sodium methylate are suspended in 250 parts by volume of benzene. 76.3 parts of thioglycollic acid methyl ester are added at room temperature. The mixture is heated to the reflux temperature, 72 parts of methyl crotonate are then added in the course of 30 minutes and refluxing is continued for 3 hours. The end product is isolated from the reaction mixture by the method described in Example 1b. 42 parts (34% of theory) of 3-hydroxy-5-methyldihydrothiophene-4-carboxylic acid methyl ester of boiling point 72°–75° C./0.035 mbar are obtained.

(b) (Reaction): 3-hydroxy-5-methylthiophene-4-carboxylic acid methyl ester

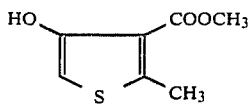

17.4 parts of 3-hydroxy-5-methyl-dihydrothiophene-4-carboxylic acid methyl ester are dissolved in 100 parts by volume of methylene chloride. 14.9 parts of sulfuryl chloride in 20 parts by volume of methylene chloride are added in the course of 30 minutes at 10° C., whilst passing nitrogen into the mixture. The end product is isolated from the reaction mixture by the method described in Example 1c. 12.9 parts (75% of theory) of 3-hydroxy-5-methyl-thiophene-4-carboxylic acid methyl ester of boiling point 67°–70° C./0.025 mbar are obtained.

EXAMPLE 10

3-Methoxythiophene-4-carboxylic acid amide

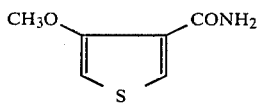

1.59 parts of 3-methoxy-dihydrothiophene-4-carboxylic acid amide are reacted with 0.88 part by volume of sulfuryl chloride in 25 parts by volume of carbon tetrachloride in the course of 2 hours at 0° C. The end product is isolated from the reaction mixture by the method described in Example 1c. 1.17 parts (75% of theory) of 3-methoxythiophene-4-carboxylic acid amide are obtained.

EXAMPLE 11

3-Acetoxy-thiophene-4-carboxylic acid methyl ester

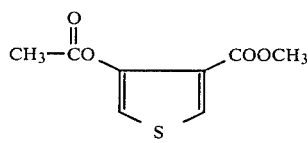

4.04 parts of 3-acetoxy-dihydrothiophene-4-carboxylic acid methyl ester are reacted with 1.76 parts by volume of sulfuryl chloride in 50 parts by volume of chloroform in the course of one hour at 0° C. The end product is isolated from the reaction mixture by the method described in Example 1c. 3.64 parts (91% of theory) of 3-acetoxy-thiophene-4-carboxylic acid methyl ester of melting point 56°–58° C. are obtained.

EXAMPLE 12

3-Thiolacetoxy-thiophene-4-carboxylic acid methyl ester

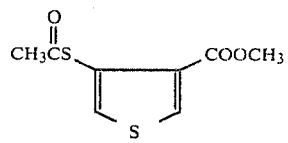

1.86 parts of 3-thiolacetoxy-dihydrothiophene-4-carboxylic acid methyl ester are reacted with 1.76 parts by volume of sulfuryl chloride in 25 parts by volume of chloroform in the course of one hour at 0° C. The end product is isolated from the reaction mixture by the method described in Example 1c. 1.4 parts (75% of theory) of 3-thiolacetoxy-thiophene-4-carboxylic acid methyl ester of melting point 92°–95° C. are obtained.

The starting material is prepared from 3-methylsulfato-dihydrothiophene-4-carboxylic acid methyl ester and potassium thiolacetate.

EXAMPLE 13

(a) (Manufacture of the starting material): 3-p-toluenesulfatodihydrothiophene-4-carboxylic acid methyl ester

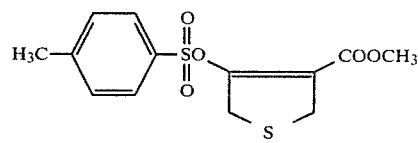

160 parts of 3-hydroxydihydrothiophene-4-carboxylic acid methyl ester and 210 parts of p-toluenesulfonyl chloride are dissolved in 500 parts by volume of pyridine at 0° C. The solution is stirred for 15 hours at from 0° to 10° C. After the reaction, the mixture is poured into 1,000 parts by volume of ice water and the batch is stirred for 30 minutes. The mixture is filtered and the filter residue is dried at 30° C. 300 parts (96% of theory) of 3-p-toluenesulfato-dihydrothiophene-4-carboxylic acid methyl ester of melting point 81°–83° C. (after recrystallization from cyclohexane) are obtained.

(b) (Manufacture of the starting material): disulfido-(3,3')-bis-(4-carbomethoxy-dihydrothiophene)

50 parts by volume of dimethylformamide and 9.52 parts of 3-p-toluenesulfato-dihydrothiophene-4-carboxylic acid methyl ester are mixed, and 3.3 parts of disodium disulfide pentahydrate are added in portions, in the course of one hour, at from 20° to 25° C. The mixture is stirred at the same temperature for a further 6 hours and is then diluted with 200 parts by volume of methylene chloride and added to 200 parts of ice water. The organic phase is separated off, washed with five times 200 parts by volume of water, filtered and concentrated. The residue is recrystallized from toluene. Yield 5.25 parts (75% of theory) of disulfido-(3,3')-bis-(4-carbomethoxydihydrothiophene) of melting point 182°–186° C.

(c) (Reaction): disulfido-(3,3')-bis-(4-carbomethoxythiophene)

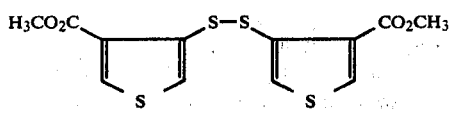

50 parts by volume of methylene chloride and 3.5 parts of disulfido-(3,3')-bis-(4-carbomethoxy-dihydrothiophene) are mixed, and 1.62 parts by volume of sulfuryl chloride are added in the course of 15 minutes at from 20° to 25° C. The reaction mixture is stirred for a further 30 minutes at the same temperature and is then diluted with 50 parts by volume of methylene chloride, washed with three times 100 parts by volume of water, dried, filtered and concentrated. Yield, 3.39 parts (98% of theory) of disulfido-(3,3')-bis-(4-carbomethoxythiophene) of melting point 92°–96° C.

EXAMPLE 14

(a) (Manufacture of the starting material): 3-methoxycarbonylmethylthiopropionic acid methyl ester

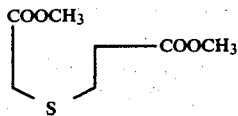

849 parts of thioglycollic acid methyl ester and 8 parts of piperidine are introduced into a stirred vessel and cooled to 10°–15° C. 758 parts of methyl acrylate are added in the course of 2 hours at from 40° to 50° C. During the reaction, a further 4 parts of piperidine are added twice. After completion of the addition, the reaction mixture is heated for 10 minutes at 60° C. and is then distilled under reduced pressure from a waterpump. 1,461 parts (95% of theory) of 3-methoxycarbonylmethyl-thiopropionic acid methyl ester of boiling point 142°–144° C./1.9 mbar are obtained.

(b) (Manufacture of the starting material): 3-hydroxydihydro-thiophene-2-carboxylic acid methyl ester

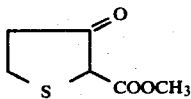

192 parts of 3-methoxycarbonylmethyl-thiopropionic acid methyl ester are added, in the course of 30 minutes, to a solution of 360 parts of a 30 percent strength by weight NaOCH₃/MeOH solution at 5° C. The resulting solution is stirred for one hour at 5° C. and then poured onto a mixture of 200 parts of concentrated hydrochloric acid and 1,000 parts of finely crushed ice. The oily layer which separates out is removed and the aqueous phase is extracted with three times 100 parts by volume of methylene chloride. The combined organic phases are extracted with three times 100 parts by volume of 5 percent strength by weight NaHCO₃ solution, dried with sodium sulfate and evaporated. The residue is distilled under reduced pressure. 140 parts (88% of theory) of 3-hydroxy-dihydrothiophene-2-carboxylic acid methyl ester of boiling point 72°–73° C./0.14 mbar are obtained.

(c) (Reaction): 3-hydroxy-thiophene-2-carboxylic acid methyl ester

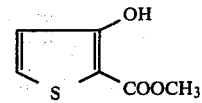

80 parts of 3-hydroxy-dihydrothiophene-2-carboxylic acid methyl ester are dissolved in 250 parts by volume of methylene chloride. 67.5 parts of sulfuryl chloride in 100 parts by volume of methylene chloride are added in the course of one hour at from 0° to 5° C., whilst passing nitrogen into the mixture. The mixture is then stirred for 2 hours at from 0° to 5° C. 50 parts of triethylamine are then added at from 0° to 5° C. and the pH is brought to 7.5 with more triethylamine. The mixture is stirred for 2 hours at 0° C. and is then brought to pH 5 by means of 10 percent strength by weight hydrochloric acid. The mixture is separated into its phases and the organic phase is washed with twice 100 parts by volume of saturated sodium chloride solution, dried, concentrated and distilled. 65 parts (82% of theory) of 3-hydroxy-thiophene-2-carboxylic acid methyl ester of boiling point 68°–73° C./0.4 mbar and melting point 42°–43° C. are obtained.

EXAMPLE 15

(a) (Manufacture of the starting material): 3-hydroxy-5-methyl-dihydrothiophene-2-carboxylic acid methyl ester

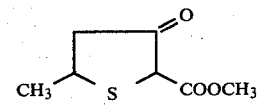

54 parts of sodium methylate are suspended in 250 parts by volume of benzene. 76.3 parts of thioglycollic acid methyl ester are added at room temperature. The mixture is heated to the reflux temperature, 72 parts of methyl crotonate are then added in the course of 30 minutes and the batch is refluxed for a further 3 hours. The mixture is poured into 150 parts by volume of ice water, the organic phase is separated off and the aqueous phase is acidified with 66 parts of glacial acetic acid and extracted with five times 100 parts by volume of methylene chloride. The combined organic phases are washed once with 100 parts by volume of water and once with 50 parts by volume of 5 percent strength by weight NaHCO₃ solution, dried and concentrated. The residue is distilled. 42 parts (34% of theory) of 3-hydroxy-5-methyldihydrothiophene-2-carboxylic acid methyl ester of boiling point 72°–75° C./0.4 mbar are obtained.

(b) (Reaction): 3-hydroxy-5-methylthiophene-2-carboxylic acid methyl ester

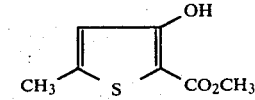

17.4 parts of 3-hydroxy-5-methyldihydrothiophene-2-carboxylic acid methyl ester are dissolved in 100 parts by volume of methylene chloride. 14.9 parts of sulfuryl chloride in 20 parts by volume of methylene chloride are added in the course of 30 minutes at 10° C., whilst passing nitrogen into the mixture. The mixture is then distilled. 12.9 parts (75% of theory) of 3-hydroxy-5-methylthiophene-2-carboxylic acid methyl ester of boiling point 67°–70° C./0.3 mbar are obtained.

EXAMPLE 16

(a) (Manufacture of the starting material): 3-(benzoylmethylthio)-propionic acid methyl ester

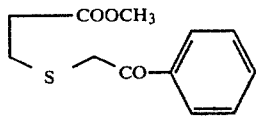

15.5 parts of chloroacetophenone are added to a solution, cooled to 0° C., of 12 parts of 3-mercapto-propionic acid methyl ester and 15.3 parts by volume of triethylamine in 100 parts by volume of chloroform. The mixture is stirred for 2 hours at 0° C. and is washed with water, and the organic phase is separated off, dried and concentrated. 21 parts (90% of theory) of 3-(benzoylmethylthio)-propionic acid methyl ester of boiling point 156°–160° C./0.3 mbar are obtained.

(b) (Manufacture of the starting material): 3-hydroxy-2-benzoyldihydrothiophene

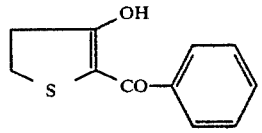

23.8 parts of 3-(benzoylmethylthio)-propionic acid methyl ester are added in the course of 30 minutes to 36 parts of a 30 percent strength by weight NaOCH₃/MeOH solution which has been cooled to 0° C., and the mixture is stirred for 2 hours at from 0° to 10° C. The end product is isolated from the reaction mixture by the method described in Example 14(b). 18.5 parts (90% of theory) of 3-hydroxy-2-benzoyldihydrothiophene of boiling point 137°–140° C./0.16-0.08 mbar are obtained.

(c) (Reaction): 3-hydroxy-2-benzoylthiophene

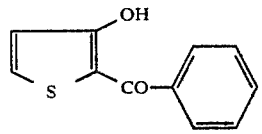

The compound is prepared by the method described in Example 14(c) from 20.6 parts of 3-hydroxy-2-benzoyldihydrothiophene and 6.75 parts of sulfuryl chloride. 16.7 parts (82% of theory) of 3-hydroxy-2-benzoylthiophene of boiling point 127°–132° C./0.5 mbar and melting point 53°–57° C. are obtained.

EXAMPLE 17

(a) (Manufacture of the starting mateial): 3-cyanomethylthiopropionic acid methyl ester

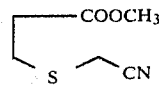

12 parts of 3-mercaptopropionic acid methyl ester and 15.3 parts by volume of triethylamine are introduced into 60 parts by volume of dried methylene chloride; a solution of 7.6 parts of chloroacetonitrile in 20 parts by volume of methylene chloride is added, at 0° C., in the course of 10 minutes and the mixture is stirred for 1.5 hours. The end product is isolated from the reaction mixture by the method described in Example 16(a). 11.9 parts (75% of theory) of 3-cyanomethylthiopropionic acid methyl ester of boiling point 95°–101° C./0.14 mbar are obtained.

(b) (Manufacture of the starting material): 3-hydroxy-2-cyanodihydrothiophene

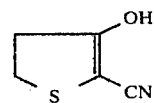

The compound is prepared by the method described in Example 16(b) from 1.59 parts of 3-cyanomethylthiopropionic acid methyl ester and 3.6 parts of a 30 percent strength by weight NaOCH₃/MeOH solution. 10.1 parts (80% of theory) of crude 3-hydroxy-2-cyanodihydrothiophene are obtained and are used, without further purification, in the next stage.

(c) (Manufacture of the starting material): 3-methoxy-2-cyanodihydrothiophene

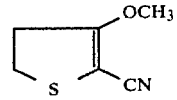

12.7 parts of 3-hydroxy-2-cyanodihydrothiophene are dissolved in 100 parts by volume of chloroform and 200 parts by volume of a 4 percent strength by weight solution of diazomethane in ether are added at 0° C. The solution is stirred for 12 hours at 0° C. and is concentrated under reduced pressure. The residue is distilled. 10.1 parts (72% of theory) of 3-methoxy-2-cyanodihydrothiophene of boiling point 82°–83° C./0.35 mbar are obtained.

(d) (Reaction): 3-methoxy-2-cyanothiophene

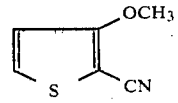

14.1 parts of 3-methoxy-2-cyanodihydrothiophene in 80 parts by volume of chloroform are reacted with 6.75 parts of sulfuryl chloride in 20 parts by volume of chloroform for 0.5 hour at 0° C. The end product is isolated from the reaction mixture by the method described in Example 14(c). 12.6 parts (91% of theory) of 3-methoxy-2-cyanothiophene of boiling point 73° C./0.16 mbar are obtained.

EXAMPLE 18

(a) (Manufacture of the starting material): 3-acetoxy-dihydrothiophene-2-carboxylic acid methyl ester

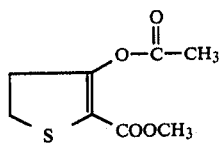

8.6 parts of acetyl chloride are added in the course of 10 minutes to a solution, cooled to 0° C., of 16 parts of 3-hydroxy-thiophene-2-carboxylic acid methyl ester and 15.3 parts by volume of triethylamine in 100 parts by volume of chloroform. The solution is stirred for 4 hours at 0° C. After the reaction, the mixture was poured into 100 parts by volume of ice water and the organic phase is separated off, dried and concentrated. The residue is distilled. 19.4 parts (96% of theory) of 3-acetoxydihydrothiophene-2-carboxylic acid methyl ester of boiling point 82°–84° C./0.08 mbar are obtained.

(b) Reaction): 3-acetoxythiophene-2-carboxylic acid methyl ester

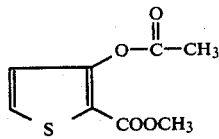

20.2 parts of 3-acetoxydihydrothiophene-2-carboxylic acid methyl ester are reacted with 6.75 parts by volume of sulfuryl chloride in 150 parts by volume of CCl$_4$ at 0° C. for one hour. The end product is isolated from the reaction mixture by the method described in Example 14(c). 15.8 parts (79% of theory) of 3-acetoxy-thiophene-2-carboxylic acid methyl ester of boiling point 84°–86° C./0.04 mbar are obtained.

EXAMPLE 19

(a) (Manufacture of the starting material): 3-methylsulfatodihydrothiophene-2-carboxylic acid methyl ester

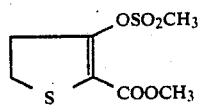

16 parts of 3-hydroxydihydrothiophene-2-carboxylic acid methyl ester and 8.6 parts by volume of methanesulfonic acid chloride are dissolved in 100 parts by volume of pyridine at 0° C. The solution is stirred for 15 hours at 0° to 10° C. After the reaction, the mixture is poured into 150 parts by volume of ice water and the batch is extracted with three times 50 parts by volume of methylene chloride. The combined organic phases are washed with twice 50 parts by volume of 10 percent strength by weight aqueous citric acid solution and three times with saturated sodium chloride solution. After drying and concentrating the organic phases, 18.8 parts (79% of theory) of 3-methylsulfatodihydrothiophene-2-carboxylic acid methyl ester of melting point 75°–77° C. are obtained.

(b) (Reaction): 3-methylsulfatothiophene-2-carboxylic acid methyl ester

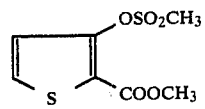

23.8 parts of 3-methylsulfatodihydrothiophene-2-carboxylic acid methyl ester are reacted with 6.75 parts by volume of sulfuryl chloride in 125 parts by volume of chloroform at 0° C. for 2 hours. The end product is isolated from the reaction mixture by the method described in Example 14(c). 19.6 parts (83% of theory) of oily 3-methylsulfatothiophene-2-carboxylic acid methyl ester are obtained.

EXAMPLE 20

(a) (Manufacture of the starting material): 3-phenylthiodihydrothiophene-2-carboxylic acid methyl ester

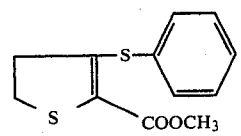

2.38 parts of 3-methylsulfatodihydrothiophene-2-carboxylic acid methyl ester are introduced into 10 parts by volume of dimethylformamide and the mixture is cooled to 0° C. 1.45 parts of sodium thiophenolate in 10 parts by volume of dimethylformamide are added in the course of 15 minutes and the reaction mixture is stirred for one hour at 0° C. It is then added to 50 parts by volume of water and extracted with three times 25 parts by volume of methylene chloride. The combined organic phases are dried and concentrated. 2.08 parts (88% of theory) of 3-phenylthiodihydrothiophene-2-carboxylic acid methyl ester of melting point 43°–45° C. are obtained.

(c) (Reaction): 3-phenylthiothiophene-2-carboxylic acid methyl ester

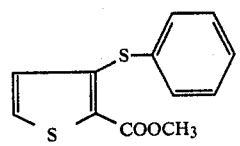

Using the method described in Example 14(c), 2.52 parts of 3-phenylthiodihydrothiophene-2-carboxylic acid methyl ester, on reaction with 0.66 part of sulfuryl chloride for 2 hours at 0° C., give 2.33 parts of 3-phenylthiophene-2-carboxylic acid methyl ester (93% of theory) of melting point 63°–66° C.

EXAMPLE 21

(a) (Manufacture of the starting material): 3-amino-2-benzoyldihydrothiophene

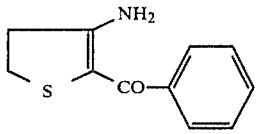

8.7 parts of β-mercaptopropionitrile are added to a solution of 2.6 parts of sodium in 175 parts by volume of methanol at 22° C., whilst stirring. After 10 minutes, 15.5 parts of chloroacetophenone at 35° C. is added in the course of 30 minutes and the temperature is maintained at 22° C. The mixture is stirred for a further 30 minutes at 22° C. and is then heated for 2 hours at 65° C. under reflux. When it has cooled, the reaction mixture is neutralized with acetic acid and is poured into 250 parts of ice water, and the batch is extracted with three times 50 parts by volume of chloroform. After evaporating the combined, dried chloroform extracts, an oily residue remains, which is triturated with 50 parts of cold alcohol and hereupon crystallizes. 17.5 parts (85% of theory) of 3-amino-3-benzoyl-dihydrothiophene of melting point 147°–149° C. are obtained.

(b) (Reaction): 3-amino-2-benzoylthiophene

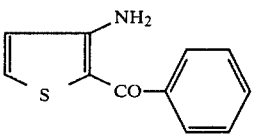

Using the method described in Example 14(c), 2.05 parts of 3-amino-2-benzoyl-dihydrothiophene, on reaction with 0.66 parts of sulfuryl chloride for one hour at 0° C., give 1.6 parts (77% of theory) of 3-amino-2-benzoyl-thiophene of melting point 100°–102° C.

EXAMPLE 22

(a) (Manufacture of the starting material): 3-acetylamino-2-benzoyldihydrothiophene

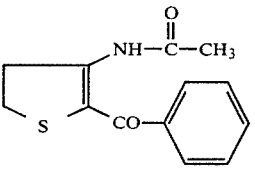

2.05 parts of 3-amino-2-benzoyl-dihydrothiophene in 10 parts by volume of acetic anhydride are heated for 2 hours at 80° C. After removing the acetic anhydride and recrystallizing the residue from ethanol, 2.3 parts (95% of theory) of 3-acetylamino-2-benzoyl-dihydrothiophene of melting point 65°–66° C. are obtained.

(b) (Reaction): 3-acetylamino-2-benzoylthiophene

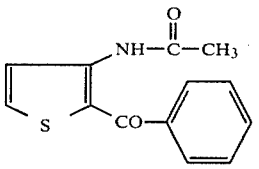

Using the method described in Example 14(c), 2.47 parts of 3-acetylamino-2-benzoyldihydrothiophene, on reaction with 0.66 parts of sulfuryl chloride for one hour at 0° C., give 2.0 parts of 3-acetylamino-2-benzoylthiophen (82% of theory) of melting point 93°–95° C.

EXAMPLE 23

(a) (Manufacture of the starting material): disulfido-(3,3')-bis(dihydrothiophene-2-carboxylic acid methyl ester)

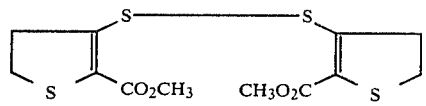

50 parts by volume of dimethylformamide and 9.52 parts of 3-methyl-sulfatodihydrothiophene-2-carboxylic acid methyl ester are mixed and 3.3 parts of disodium disulfide.5H$_2$O are added in portions over one hour, at from 20° to 25° C. The mixture is stirred for 6 hours at 0° C., diluted with 200 parts by volume of methylene chloride and and poured into 200 parts of ice water. The organic phase is separated off, washed with five times 200 parts by volume of water, dried with sodium sulfate, filtered off and concentrated. The residue is recrystallized from toluene. 5.25 parts (75% of theory) of disulfido-(3,3')-bis(-dihydrothiophene)-2-carboxylic acid methyl ester) of melting point 133°–137° C. are obtained.

(b) (Reaction): disulfido-(3,3')-bis-(thiophene-2-carboxylic acid methyl ester)

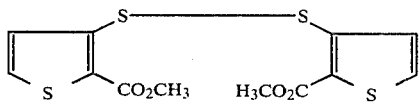

50 parts by volume of methylene chloride and 3.5 parts of disulfido-(3,3')-bis-(dihydrothiophene-2-carboxylic acid methyl ester) are mixed and 1.62 parts by volume of sulfuryl chloride are added in the course of 15 minutes at from 20° to 25° C. The reaction mixture is stirred for 30 minutes at 23° C., diluted with 50 parts by volume of methylene chloride, washed with three times 100 parts by volume of water, dried with sodim sulfate, filtered off and concentrated. 3.39 parts (98% of theory) of disulfido-(3,3')-bis-(thiophene-2-carboxylic acid methyl ester) of melting point 141°–145° C. are obtained.

We claim:

1. Thiophene compounds of the formula

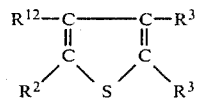

where $R^{12}$ is

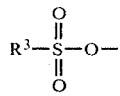

$R^2$ is —CN the individual radical $R^3$ may be identical or different and each is an an aliphatic, cycloaliphatic, araliphatic or aromatic radical, and $R^3$ may also be hydrogen.

* * * * *